United States Patent
Özer et al.

(10) Patent No.: US 12,067,086 B2
(45) Date of Patent: Aug. 20, 2024

(54) FEATURE DATASET CLASSIFICATION

(71) Applicant: ARM LIMITED, Cambridge (GB)

(72) Inventors: Emre Özer, Cambridge (GB); Gavin Brown, Cambridge (GB); Charles Edward Michael Reynolds, Cambridge (GB); Jedrzej Kufel, Cambridge (GB); John Philip Biggs, Cambridge (GB)

(73) Assignee: Arm Limited, Cambridge (GB)

( * ) Notice: Subject to any disclaimer, the term of this patent is extended or adjusted under 35 U.S.C. 154(b) by 187 days.

(21) Appl. No.: 17/593,716

(22) PCT Filed: Feb. 27, 2020

(86) PCT No.: PCT/GB2020/050469
§ 371 (c)(1),
(2) Date: Sep. 23, 2021

(87) PCT Pub. No.: WO2020/201684
PCT Pub. Date: Oct. 8, 2020

(65) Prior Publication Data
US 2022/0156531 A1    May 19, 2022

(30) Foreign Application Priority Data
Mar. 29, 2019 (GB) ..................................... 1904481

(51) Int. Cl.
*A61B 5/00* (2006.01)
*G06F 18/214* (2023.01)
(Continued)

(52) U.S. Cl.
CPC ...... *G06F 18/24155* (2023.01); *A61B 5/6801* (2013.01); *A61B 5/6813* (2013.01);
(Continued)

(58) Field of Classification Search
CPC .......... G06N 20/00; G06N 3/045; G06N 3/02; G06N 3/08; G06N 3/088; G06N 20/20;
(Continued)

(56) References Cited

U.S. PATENT DOCUMENTS

| 2005/0085133 A1* | 4/2005 | Wang | ...................... H01R 24/62 |
| | | | 439/660 |
| 2006/0292572 A1* | 12/2006 | Stuart | .................... G16B 20/30 |
| | | | 435/6.14 |

(Continued)

FOREIGN PATENT DOCUMENTS

WO    WO-2007029002 A2 *   3/2007    ........... G06F 16/683

OTHER PUBLICATIONS

Wang et al., Deep sketch feature for cross-domain image retrieval, Neurocomputing, Sep. 26, 2016 [retrieved Apr. 29, 2023], vol. 207, pp. 387-397. Retrieved: https://www.sciencedirect.com/science/article/pii/S0925231216303198 (Year: 2016).*

(Continued)

*Primary Examiner* — Matthew C Bella
*Assistant Examiner* — Dennis Rosario
(74) *Attorney, Agent, or Firm* — NIXON & VANDERHYE P.C.

(57) ABSTRACT

Apparatuses and methods of operating such apparatuses are disclosed. An apparatus comprises feature dataset input circuitry to receive a feature dataset comprising multiple feature data values indicative of a set of features, wherein each feature data value is represented by a set of bits. Class retrieval circuitry is responsive to reception of the feature dataset from the feature dataset input circuitry to retrieve from class indications storage a class indication for each feature data value received in the feature dataset, wherein class indications are predetermined and stored in the class indications storage for each permutation of the set of bits for (Continued)

each feature. Classification output circuitry is responsive to reception of class indications from the class retrieval circuitry to determine a classification in dependence on the class indications. A predicated class may thus be accurately generated from a simple apparatus.

17 Claims, 10 Drawing Sheets

(51) Int. Cl.
  *G06F 18/2415* (2023.01)
  *G06F 18/25* (2023.01)
  *G16H 10/65* (2018.01)
  *G16H 40/60* (2018.01)

(52) U.S. Cl.
  CPC ............ *G06F 18/214* (2023.01); *G06F 18/25* (2023.01); *A63B 2220/836* (2013.01); *G06F 18/259* (2023.01); *G16H 10/65* (2018.01); *G16H 40/60* (2018.01)

(58) Field of Classification Search
  CPC ........ G16H 10/60; G16H 10/65; G16H 10/40; G16H 50/30; G16H 50/70; G16H 40/60; A61B 2562/00; A61B 5/14532; A61B 5/318; A61B 5/002; A61B 5/02405; A61B 5/6801; A61B 5/68; A61B 5/6824; A61B 5/6823; A61B 5/6813; A61B 5/021; A61B 5/0816; A61B 5/0833; A61B 5/6804; A61B 5/6803; A61B 5/681; A61B 5/024; A61B 5/6833; A61B 5/683; A63B 2024/0065; A63B 2230/06; A63B 2230/04; A63B 2230/50; A63B 2220/836; G06V 10/7715
  See application file for complete search history.

(56) References Cited

U.S. PATENT DOCUMENTS

| | | | | |
|---|---|---|---|---|
| 2008/0180287 A1* | 7/2008 | Widmer | .................. | H03M 7/20 341/95 |
| 2008/0275309 A1* | 11/2008 | Stivoric | ................. | G16H 10/60 600/300 |
| 2013/0132377 A1* | 5/2013 | Lin | ........................ | G06F 16/583 707/723 |
| 2019/0080450 A1* | 3/2019 | Arar | ...................... | G06V 20/695 |
| 2019/0147296 A1* | 5/2019 | Wang | ................... | G06F 18/2148 382/157 |
| 2019/0247650 A1* | 8/2019 | Tran | ...................... | A61N 1/3704 |
| 2019/0272341 A1* | 9/2019 | Lu | .......................... | G06F 16/325 |

OTHER PUBLICATIONS

Yildrim et al., Naive Bayes classifier for continuous variables using novel method (NBC4D) and distributions, 2014 IEEE International Symposium on Innovations in Intelligent Systems and Applications (INISTA) Proceedings, Jun. 23-25, 2014 [retrieved Apr. 29, 2023], 6 pages. Retrieved: (Year: 2014).*

[Item V continued] https://ieeexplore.ieee.org/abstract/document/6873605 (Year: 2014).*

Carvalho et al., Combining Boolean Neural Architectures for Image Recognition, 1997 [retrieved Apr. 29, 2023], Connection Science, vol. 9, No. 4, 1997, 15 pages. Retrieved: https://www.tandfonline.com/doi/abs/10.1080/095400997116612 (Year: 1997).*

Jabo, Machine Vision for Wood Defect Detection and Classification [Thesis], 2011 [retrieved Apr. 5, 2024], Chalmers University of Technology, 116 pages. Retrieved: https://odr.chalmers.se/server/api/core/bitstreams/72a52bb4-f63f-46dd-9963-cfbd62d6e3b9/content (Year: 2011).*

Anonymous: "ASCII—Wikipedia", Feb. 7, 2019 (Feb. 7, 2019), XP055689521, Retrieved from the Internet: URL: https://en.wikipedia.org/w/index.php?title=ASCII&oldid=882225814 [retrieved on Apr. 27, 2020] p. 1 par 1. p. 2 par 1.

Anonymous: "Program to implement ASCII lookup table—Geeksfor Geeks", Dec. 11, 2015 (Dec. 11, 2015), XP055689525, Retrieved from the Internet: URL:https://www.geeksforgeeks.org/program-implement-ascii-lookup-table/ [retrieved on Apr. 27, 2020] p. 1 par 1.

* cited by examiner

FEATURE DATASET CLASSIFICATION

The present techniques relate to the field of data processing.

Various approaches may be taken to classify an input data set on the basis of a number of feature data values which make up that feature data set. For example an apparatus may be constructed on the basis of naive Bayes classifiers which apply Bayes' Theorem. A common implementation is based on the Gaussian naïve Bayes algorithm, in which each factor of the likelihood term in the Bayes equation is modelled as a (univariate) Gaussian distribution. A naïve Bayes algorithm implementation can be trained using training data sets (in which the desired class to be predicted is known) and then this trained model can be used for new input data sets to generate class predictions. Such an implementation may, in hardware, still require a significant level of computation ability in order to process each input data set and generate the predicted class on the basis of the trained model. There may be some implementation contexts in which it is desirable for the class prediction to be generated by a simpler device with limited data processing ability.

At least some examples provide an apparatus comprising: feature dataset input circuitry to receive a feature dataset comprising multiple feature data values indicative of a set of features, wherein each feature data value is represented by a set of bits; class retrieval circuitry responsive to reception of the feature dataset from the feature dataset input circuitry to retrieve from class indications storage a class indication for each feature data value received in the feature dataset, wherein class indications are predetermined and stored in the class indications storage for each permutation of the set of bits for each feature; and classification output circuitry responsive to reception of class indications from the class retrieval circuitry to determine a classification in dependence on the class indications.

At least some examples provide a method of operating an apparatus comprising: receiving at a feature dataset input a feature dataset comprising multiple feature data values indicative of a set of features, wherein each feature data value is represented by a set of bits; retrieving from class indications storage a class indication for each feature data value received in the feature dataset, wherein class indications are predetermined and stored in the class indications storage for each permutation of the set of bits for each feature; and determining a classification in dependence on the class indications.

At least some examples provide an apparatus comprising: means for receiving a feature dataset comprising multiple feature data values indicative of a set of features, wherein each feature data value is represented by a set of bits; means for retrieving from means for storing class indications a class indication for each feature data value received in the feature dataset, wherein class indications are predetermined and stored in the means for storing class indications for each permutation of the set of bits for each feature; and means for determining a classification in dependence on the class indications.

The present techniques will be described further, by way of example only, with reference to embodiments thereof as illustrated in the accompanying drawings, to be read in conjunction with the following description, in which.

In one example herein there is an apparatus comprising: feature dataset input circuitry to receive a feature dataset comprising multiple feature data values indicative of a set of features, wherein each feature data value is represented by a set of bits; class retrieval circuitry responsive to reception of the feature dataset from the feature dataset input circuitry to retrieve from class indications storage a class indication for each feature data value received in the feature dataset, wherein class indications are predetermined and stored in the class indications storage for each permutation of the set of bits for each feature; and classification output circuitry responsive to reception of class indications from the class retrieval circuitry to determine a classification in dependence on the class indications.

Before discussing features of the present techniques, for context the core features of the Naïve Bayes algorithm are first outlined. Naïve Bayes is a probabilistic machine learning algorithm based on the application of Bayes' Theorem. It uses the simplifying assumption that all features are statistically independent once conditioned on the value of the class label. This simplifies the Bayes equation into the following:

$$y^* = \operatorname*{argmax}_{y \in Y} \frac{p(y) \prod_{i=1}^{d} p(x_i | y)}{p(x)} \quad \text{Equation 1}$$

$y^*$ is the class label that maximises the equation where $Y = \{\text{set of classes}\}$, and d is the number of features, and $x_i$ are the observed feature values. $p(y)$ are the priors, and $\prod_{i=1}^{d} p(x_i|y)$ is the likelihood function. The denominator term may be omitted, because it has no effect on the maximum, and the logarithm is taken to turn multiplications into additions:

$$y^* = \underset{y \in Y}{\operatorname{argmax}}\left[\log p(y) + \sum_{i=1}^{d} \log p(x_i \mid y)\right].\quad\text{Equation 2}$$

Gaussian Naïve Bayes is a variant in which each factor of the likelihood term is modelled as a (univariate) Gaussian distribution:

$$p(x \mid y) = \frac{1}{\sigma\sqrt{2\pi}}e^{-\frac{(x-\mu)^2}{2\sigma^2}}\quad\text{Equation 3}$$

If the features are assumed to follow the Gaussian distribution, then each likelihood term will be substituted by the Gaussian probability density function as follows:

$$y^* = \underset{y \in Y}{\operatorname{argmax}}\left[\log p(y) + \sum_{i=1}^{d}\left[-\log \sigma_{y,i}\sqrt{2\pi} - \frac{x_i - \mu_{y,i}}{2\sigma_{y,i}^2}\right]\right].\quad\text{Equation 4}$$

Eventually, this reduces to a simple form like the equation below:

$$y^* = \arg\max_{y \in Y}[C_y + \Sigma_{i=1}^{d}[K0_{y,i} + K1_{y,i} \cdot x_i + K2_{y,i} \cdot x_i^2]]\quad\text{Equation 5}$$

where $C_y$ is the log prior of the class, and $K0_{y,i}$, $K1_{y,i}$ and $K2_{y,i}$ are constant and coefficients for each class/feature combination. Generally, although these values can be pre-computed in a training stage, and stored in memory, calculating the class probabilities is still compute-intensive requiring multiple MAC operations.

In this context the present techniques provide an apparatus which receives a feature data set comprising multiple feature data values and on the basis of that received feature data set determines a classification (i.e. a class) representative of that feature data set. However, instead of accumulating all of the features to find the probability of each possible class, and then determining the class with the maximum probability, an approach is proposed in which class probabilities for each possible value of each feature are precomputed. That is to say in the classifier apparatus proposed, instead of considering a single classifier with multiple features, multiple distinct classifiers are generated and from those one is selected to be the representative class. The inventors of the present techniques have established that in an apparatus implementing this approach this can enable the gate count to be reduced, and potentially make the operation of class determination faster.

In some embodiments the class indications stored in the class indications storage for each feature are each predetermined as a best class indication which maximises a Bayes Classifier for the feature in a training phase using feature training datasets. Accordingly, the class probabilities for each feature are precomputed in the training phase and the best class for that feature can then be selected under its corresponding Bayes classifier:

$$\hat{y}_i = \underset{y \in Y}{\operatorname{argmax}}[C_y + K0_{y,i} + K1_{y,i} \cdot x_i + K2_{y,i} \cdot x_i^2],\quad\text{Equation 6}$$

Various forms of Bayes classifier may be implemented, but in some embodiments the Bayes Classifier is a Gaussian naïve Bayes Classifier.

Each feature of the set of features may be modelled using a range of different distribution types. In some embodiments the Bayes Classifier is based on a single distribution type used for each feature of the set of features. In some embodiments the Bayes Classifier is based on heterogeneous distribution types used for the set of features. These distribution types may take a variety of forms such as for example Gaussian, exponential, uniform and so on. The approach proposed does not constrain each feature to come from a particular type of distribution or for all features to come from the same type of distribution, which allows more flexibility in the implementation, for example if exact distributions of the features are known.

The retrieval of the class indications from the class indication storage may take a variety of forms but in some embodiments the class indications storage has a look-up table format and the class retrieval circuitry is arranged to perform a look-up procedure with respect to the look-up table format for each feature data value received in the feature dataset. This allows for a ready retrieval of precomputed class indications.

In some embodiments the class retrieval circuitry is arranged to retrieve in parallel the class indications for each feature data value received in the feature dataset. In some embodiments the class retrieval circuitry is arranged to retrieve in a serial sequence the class indications for each feature data value received in the feature dataset. Accordingly, it may be selected between the two different approaches, in dependence on the relative priority in a given implementation of the greater storage required when class indications are to be retrieved in parallel versus the longer retrieval time required for the class indications to be retrieved in a serial sequence.

Once the class indications have been retrieved from the class indications storage in the class retrieval circuitry, the final classification may be determined in a variety of ways, but in some embodiments the classification output circuitry is responsive to reception of the class indications from the class retrieval circuitry to determine the classification by a vote amongst the class indications. The vote itself may have a variety of configurations, but for example the class selected may be that which is the most frequent class amongst the class indications retrieved by the class retrieval circuitry. In other words it may be the statistical mode of the set of class indications.

In some embodiments the class indications are weighted. This allows for a further degree of control over the final classification selected. This weighting may be predetermined in the sense that it is pre-calculated, for example where weights for the class indications are determined in a training phase using feature training datasets. Alternatively these weights may be independently user defined. This allows greater user control over the allocation and selection of the classes.

In some embodiments weights of the class indications are used as a tiebreaker when the vote selects more than one class indication. Thus where selection between the class indications to determine a unique class indication is not possible on the basis of the vote, for example because more than one class has been selected the same number of times in the process, then weights of the class indications may be used as tiebreaker in this situation to decide between them.

The inventors of the present techniques have found that successful implementations, in the sense that they maintain a usefully high prediction accuracy for the predicted class of a given input future data sets, can be maintained even when each feature data value is represented at a low precision. For example in some embodiments each feature data value is represented by a set of fewer than 10 bits. Further, in some embodiments each feature data value is represented by a set of 5 bits.

In some embodiments the class indications are stored in the class indications storage using a representation of fewer than 5 bits. In some embodiments the class indications are stored in the class indication storage using a representation of 3 bits (i.e. allowing 8 different classes to be defined).

The present techniques may find applicability in a wide variety of contexts, but where they may be implemented in a notably low-complexity manner (in particular in terms of the gate count required) the techniques may find implementation in portable and indeed in wearable contexts. Accordingly, in some embodiments the apparatus is a wearable device.

The feature data set input may be provided from a variety of sources, but in some embodiments the feature dataset input is coupled to a plurality of sensors each providing a respective feature data value.

In some embodiments the apparatus is embodied as a plastic fabricated device. Such a data processing device, embodied in plastic (as opposed to for example being embodied as a silicon-based device), may make it particularly suitable for implementation as a wearable device, whether embedded in clothing or worn next to the skin for example.

The above mentioned low gate count of the apparatus may for example be noted in some embodiments in which the apparatus is embodied comprising fewer than 1000 logic gates. Further, in some embodiments the apparatus is embodied comprising fewer than 500 logic gates.

In one example herein there is a method of operating an apparatus comprising: receiving at a feature dataset input a feature dataset comprising multiple feature data values indicative of a set of features, wherein each feature data value is represented by a set of bits; retrieving from class indications storage a class indication for each feature data value received in the feature dataset, wherein class indications are predetermined and stored in the class indications storage for each permutation of the set of bits for each feature; and determining a classification in dependence on the class indications.

In one example herein there is an apparatus comprising: means for receiving a feature dataset comprising multiple feature data values indicative of a set of features, wherein each feature data value is represented by a set of bits; means for retrieving from means for storing class indications a class indication for each feature data value received in the feature dataset, wherein class indications are predetermined and stored in the means for storing class indications for each permutation of the set of bits for each feature; and means for determining a classification in dependence on the class indications.

Some particular embodiments are now described with reference to the figures.

Figure 1:
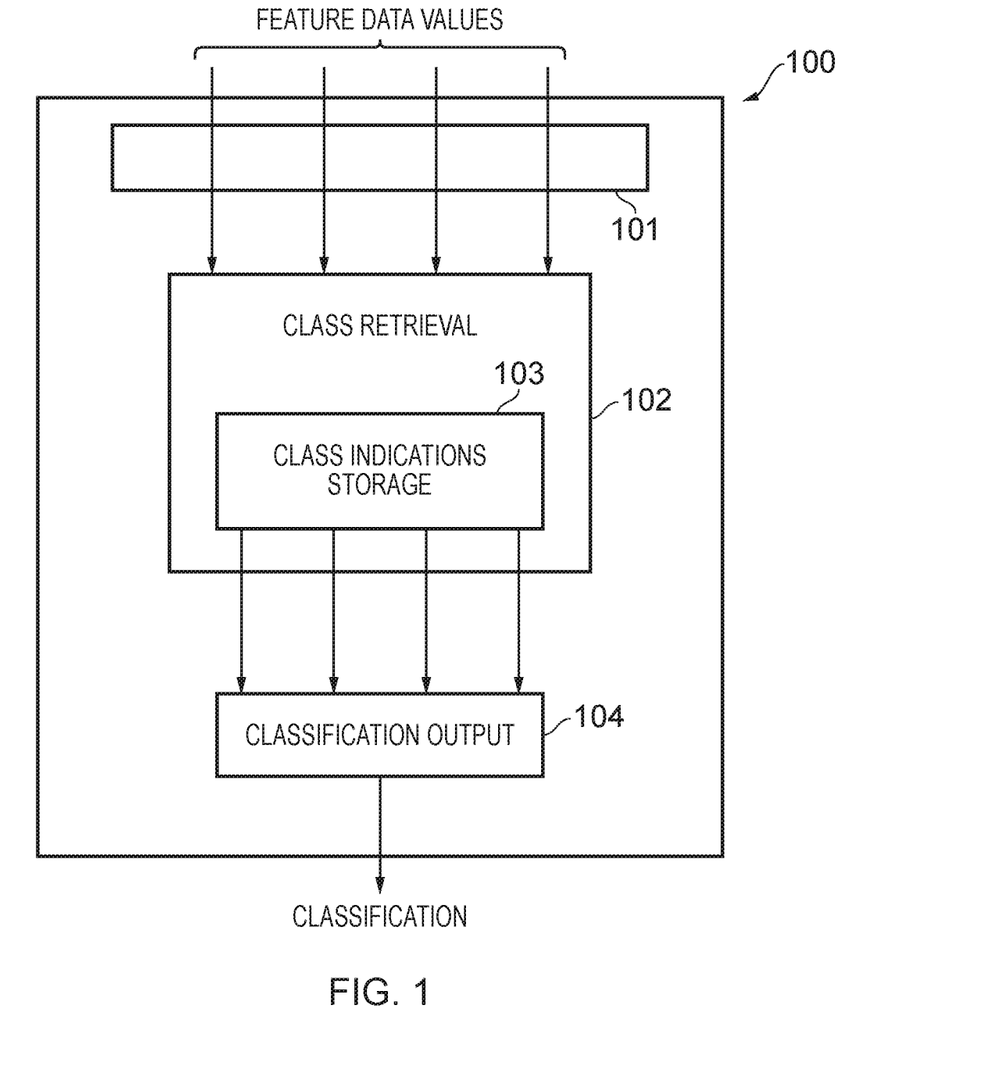
FIG. 1 schematically illustrates an apparatus according to some example embodiments.

FIG. 1 schematically illustrates an apparatus 100 in some example embodiments. The apparatus comprises feature dataset input circuitry 101 which receives a set of feature data values. Four feature data values are shown in FIG. 1 (and for simplicity and clarity of illustration this example number of inputs is continued through various example embodiments illustrated and discussed here), but the present techniques are not limited to this number of inputs in the feature dataset. This feature data set comprising multiple feature data values is passed to class retrieval circuitry 102 which uses the individual feature data values to retrieve a corresponding set of class indications from class indications storage 103. These class indications are then passed to classification output circuitry 104 which determines a final, single predicated classification based on that set of class indications received from the class retrieval circuitry 102. The final classification may be output from the apparatus 100 (as shown in FIG. 1), but in other embodiments this classification may be utilised within the apparatus 100, for example to generate an indication which a user can perceive. The class indications stored in the class indications storage are predetermined during a training phase for the apparatus, during which feature training data sets are used. This will be described in more detail with respect to FIG. 2.

Figure 2:
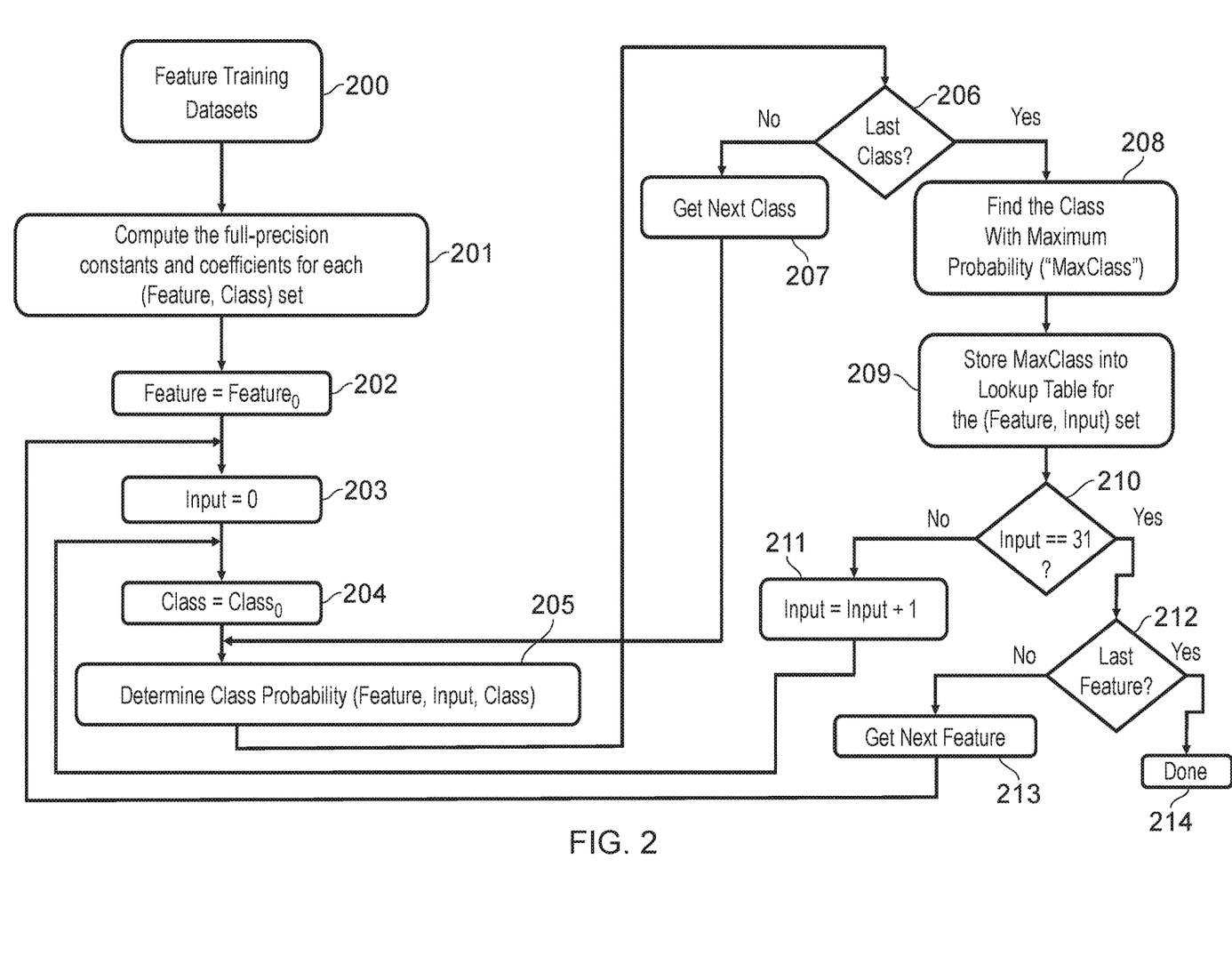
FIG. 2 schematically illustrates a training arrangement according to which a Gaussian naïve Bayes model implementation is trained using feature training data sets in some example embodiments.

FIG. 2 schematically illustrates a process for carrying out a training phase according to which a model (specifically the machine learning algorithm of the present techniques based on a modified Gaussian naïve Bayes model) is trained before being used. It should be understood that this part of the training process is carried out, for example, on a general purpose computing device and not on an apparatus such as that illustrated in FIG. 1. As shown in FIG. 2, at step 200 various feature training data sets are used as inputs. Then for each combination of feature and class, at step 201 full precision constants and coefficients are computed. An iterative process then begins to step though each feature and class to determine the respective class probabilities (see Equation 6 above) for each possible input value. Note that in this example the inputs will be quantized to a 5-bit value (though the present techniques are not limited to this quantization of input value), so there are 32 possible input values for each input. The inventors of the present techniques have found that the class prediction accuracy drops only by around 1% when such quantised input values are used. Hence at the first iteration at step 202 the first feature (Feature$_0$), at step 203 the first input (Input=0), and at step 204 the first class (Class$_0$) are set to be considered. For these parameters, at step 205, the corresponding class probability is determined (see Equation 6 above). It is then checked at step 206 if all classes (for this feature and input value combination) have now been considered. In some embodiments described here there are 8 classes (though the present techniques are not limited to this particular number of classes). Whilst they have not, step 207 gets the next class to consider and the flow returns to step 205. Once all class probabilities for all classes (for this feature and input combination) have been determined the flow proceeds to step 208, where the class with the maximum probability is found. This class ("MaxClass") is then stored into class indications storage, such as a lookup table for this feature and input value combination at step 209. At step 210 it is then determined if the last input value (in this 5-bit example, this being number 31) has been reached. Whilst it has not step 211 increments the input value and the flow returns to step 204. Once the last input value has been reached the flow proceeds to step 212, where it is determined if the last feature of the set has been reached. Whilst it has not step 213 gets the next feature to consider and the flow returns to step 203. Once the last features has been reached, then the full set of iterations (over features, input values and classes) is complete the flow of the training process concludes at step 214.

An algorithm is used by the present techniques, according to which instead of considering a single naïve Bayes classifier with d features, d distinct Bayes classifiers are considered and their predictions are aggregated to select the final classification. A useful characteristic is that each feature (represented by a feature value) may derive from a completely different distribution (e.g. Gaussian, exponential, uniform, etc.).

Figure 3A:
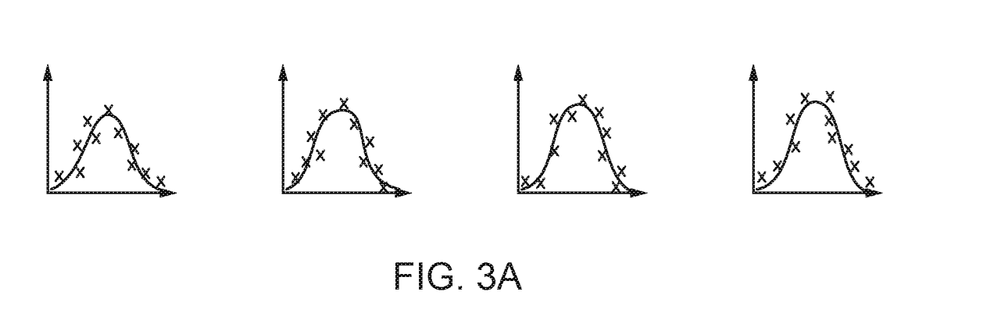
FIGS. 3A and 3B show examples feature distributions on which the trained model may be based in some example embodiments.
Figure 3B:
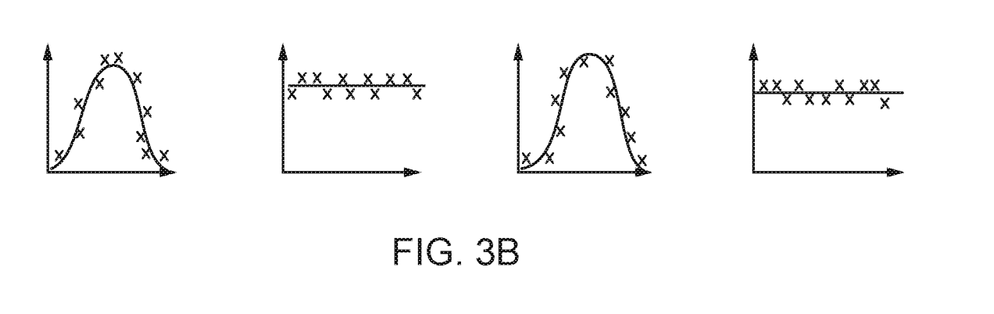

FIG. 3A shows an example set of distributions according to which each of four feature value data sets are assumed to be represented by Gaussian distributions, whilst FIG. 3B shows a set of four feature value distributions in which two are Gaussian distributions and two are uniform distributions.

Figure 4:
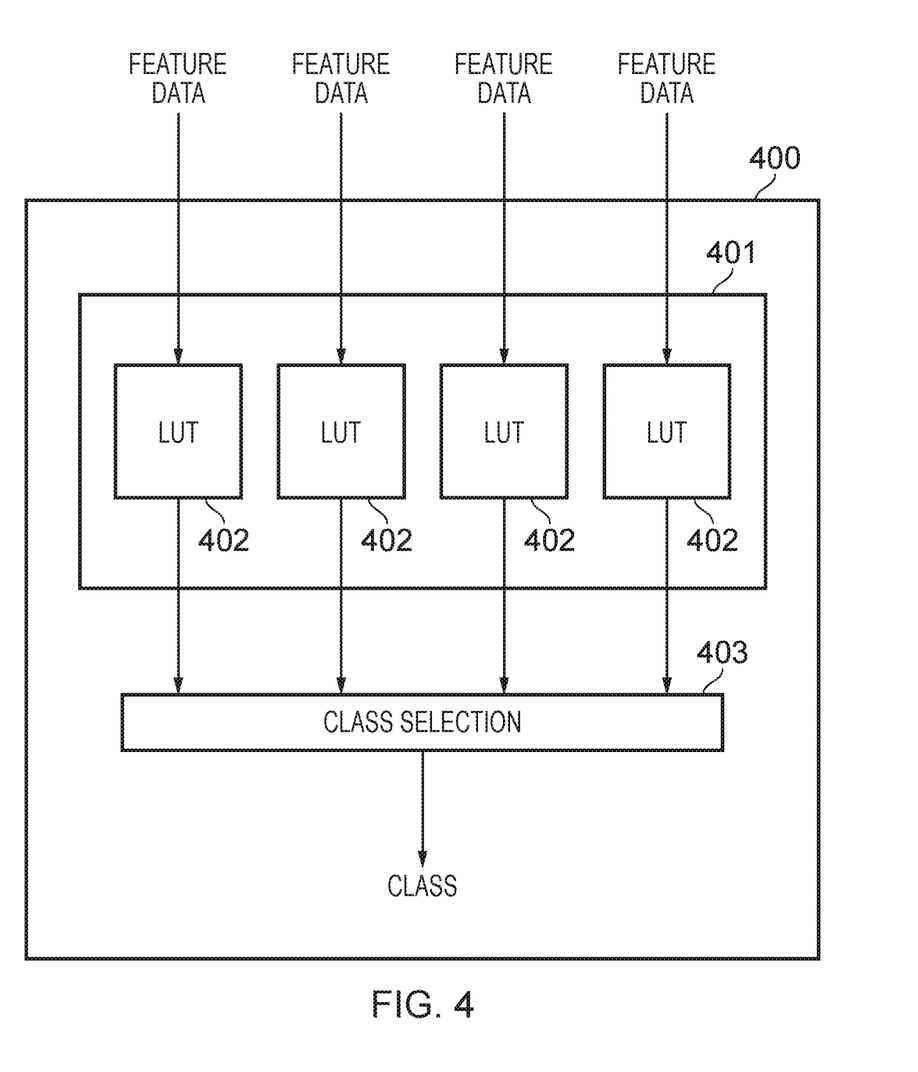
FIG. 4 schematically illustrates an apparatus comprising multiple class lookup tables which are accessed in parallel in some example embodiments.

FIG. 4 schematically illustrates an apparatus 400 in some example embodiments. Here the class retrieval circuitry 401 comprises 4 lookup tables (LUT) 402, one of which is provided for each feature data value which the apparatus is configured to receive—note that in this example the feature dataset input circuitry is not explicitly represented. Accordingly, on receipt of a feature data set, each feature data value is used in a lookup in a respective LUT 402 and a class indication from each is read out. This set of class indications is then passed to class selection circuitry 304 which selects a single representative class on the basis of the class indications received.

Figure 5:
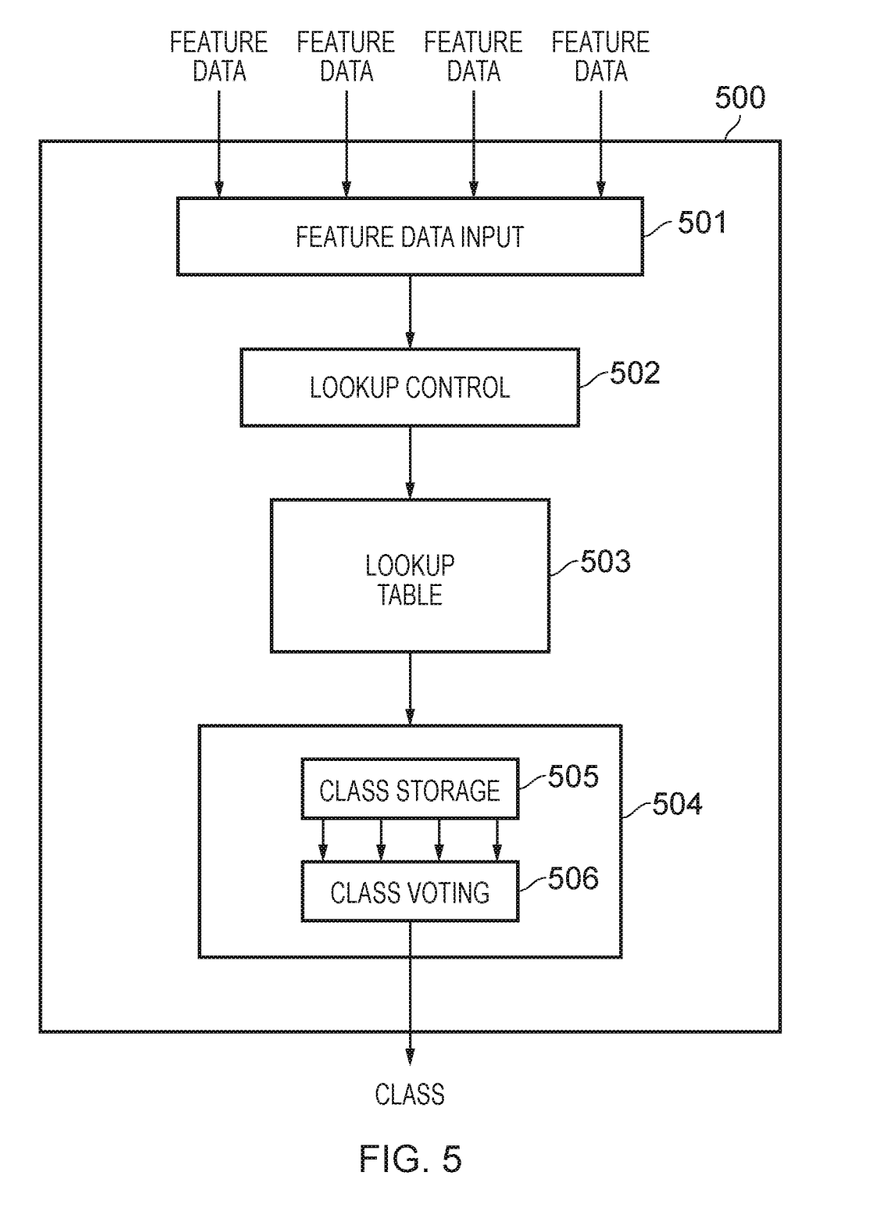
FIG. 5 schematically illustrates an apparatus comprising a single class lookup table which is serially accessed for multiple feature values in some example embodiments.

FIG. 5 schematically illustrates an apparatus 500 in some example embodiments. Feature data values are received by a feature data input data 501 which holds these values such that the lookup control circuitry 502 can make use of them in sequence to perform a lookup in the single lookup table 503. That is to say four lookups in the lookup table 503 are performed in a serial sequence under the control of the lookup control 502 using the four feature data values received. The result of each lookup in the lookup table 503 is passed to the class determination circuitry 504 where, whilst the serial lookup procedure is being carried out, the classes received are temporarily stored in class storage 505. From here they are then retrieved for the class voting circuitry 506 to determine a single class for output on the basis of a vote between them. Here the vote is performed by majority in the sense that the most common (mode) class is selected as the winning class for output.

Figure 6A:
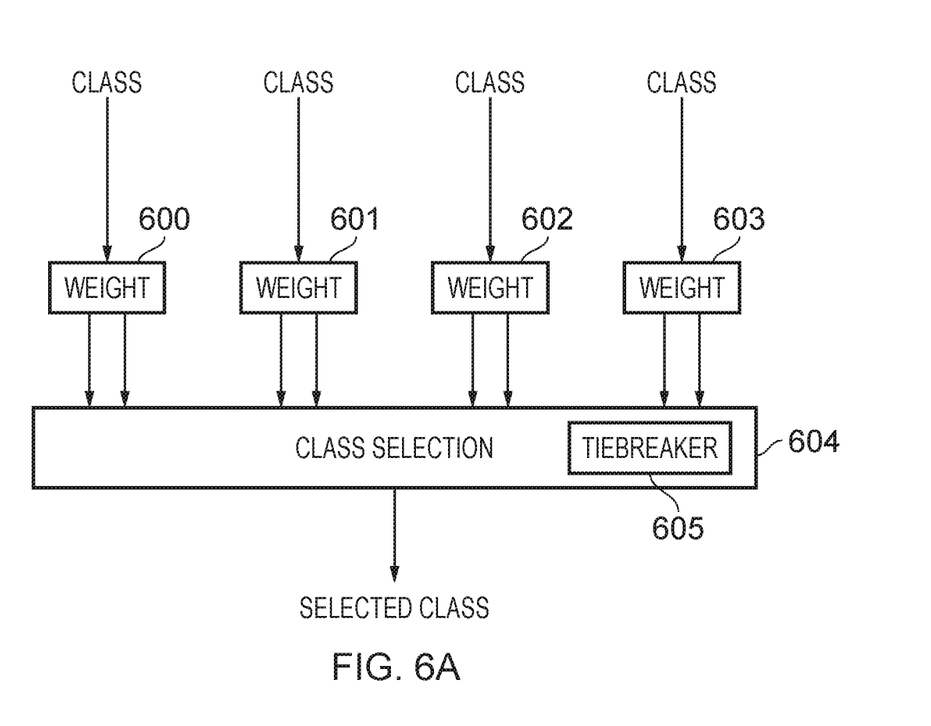
FIG. 6A schematically illustrates the weighting of class values in some example embodiments.
Figure 6B:
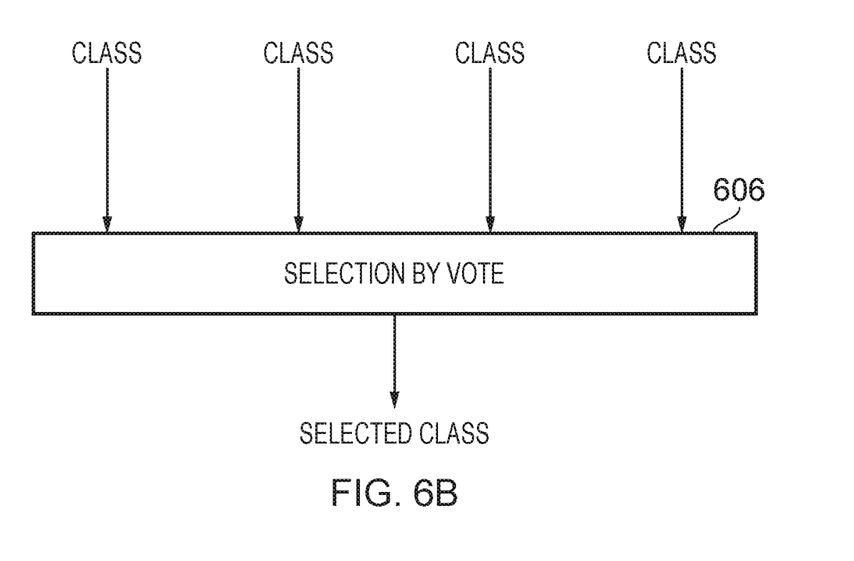
FIG. 6B schematically illustrates a selection between indicated classes by vote in some example embodiments.

FIG. 6A schematically illustrates one example embodiment in which weights 600-603 are associated with the classes retrieved from the class indication storage before a class selection takes place. These weights may be learnt as part of the training, as for example carried out as shown in FIG. 2, or may be explicitly set by a user, wishing to influence the balance of the class selection. Hence, for each class received from the class indications storage (e.g. a lookup table) an associated weight is used for each. The weights can be stored in the same lookup table as the classes or they can be in a separate storage. It is to be noted therefore that this weight is thus effectively applied for the "importance" of each respective feature data value, but the class values themselves are not amended since these are integer values used for enumerating the set of possible classes. Each class and its associated weight are then received by the class selection circuitry 604 which performs a determination of the selected class on the basis of the distribution of classes themselves, and their associated weights. For example, the weights may indicate the relative voting weight that each feature data value thus has in the final selection. Additionally, or as an alternative, the class selection circuitry 604 may comprise tie breaker circuitry 605 which can make use of the weight in the event that a tie break is necessary. A tie break occurs when the selection procedure (e.g. mode voting) cannot differentiate between two or more selected classes. In this instance the respective associated weights may be used as a tie break influence. As mentioned above the selection between the class indications received from the class indication storage may take a variety of forms, but in some embodiments such as that illustrated in FIG. 6B, this selection is by vote, for example by mode vote.

Figure 7:
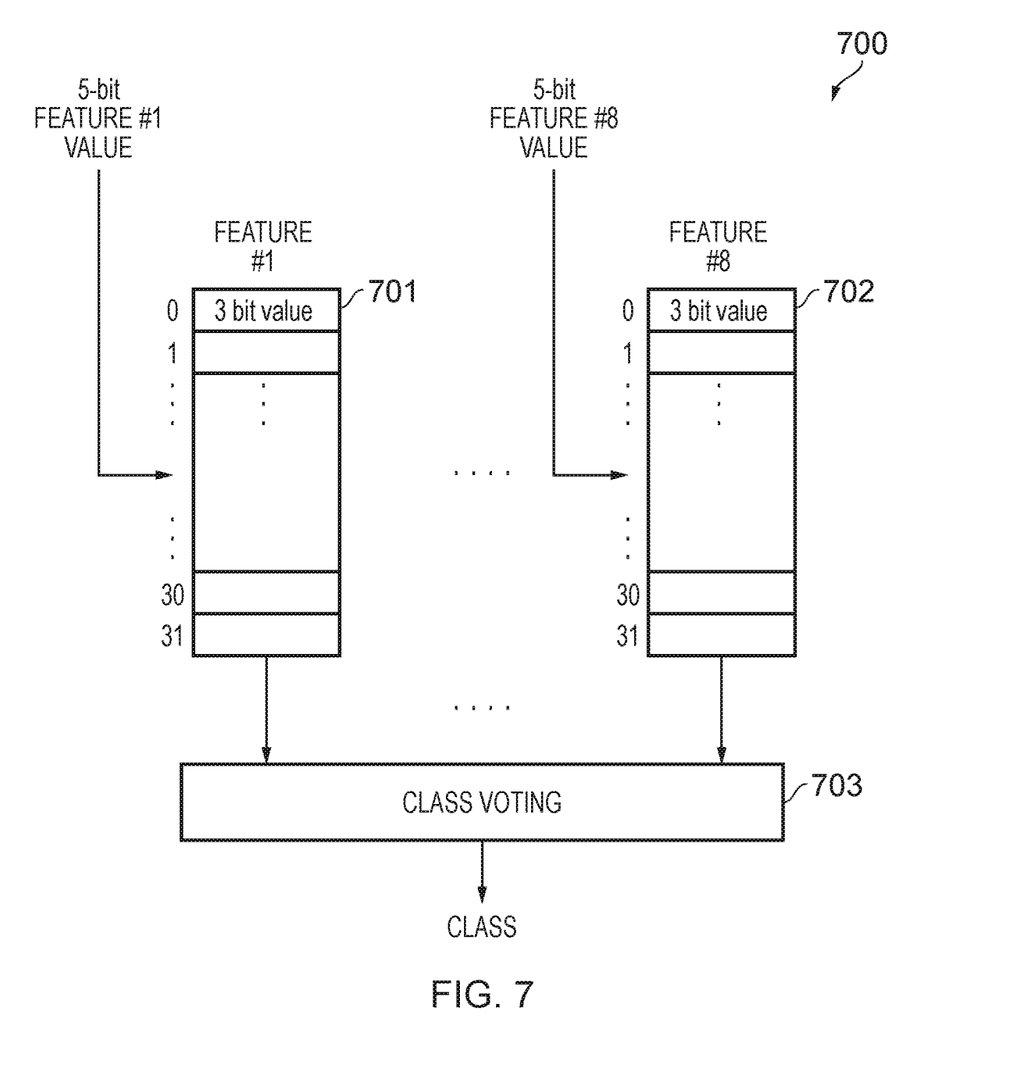
FIG. 7 schematically illustrates a low precision implementation for receiving 5-bit feature values to be used to lookup 3-bit class values in some example embodiments.

FIG. 7 schematically illustrates some components of an apparatus 700 in one embodiment. In this example eight feature data values are received, each quantised into 5-bit values. These respective 5-bit values are used to perform lookups in a corresponding set of eight lookup tables (of which only two 701 and 702 have been explicitly shown, purely of the sake of clarity) which have each been pre-populated (in a training phase) with 3-bit class indications for each possible value of each feature value. In other words, there are 32 entries in each lookup table. Hence, eight lookup actions are performed in parallel to retrieve eight 3-bit class values which are passed to the class voting circuitry 703. The class voting circuitry 703 then performs the final selection of the class prediction which in this example is on the basis of a mode vote amongst the eight class indications received. An implementation such at that shown in FIG. 7 (using the new algorithm described herein) has been demonstrated to have a class prediction accuracy of 91%, which is very close to the accuracy of the Gaussian naïve Bayes.

Figure 8A:
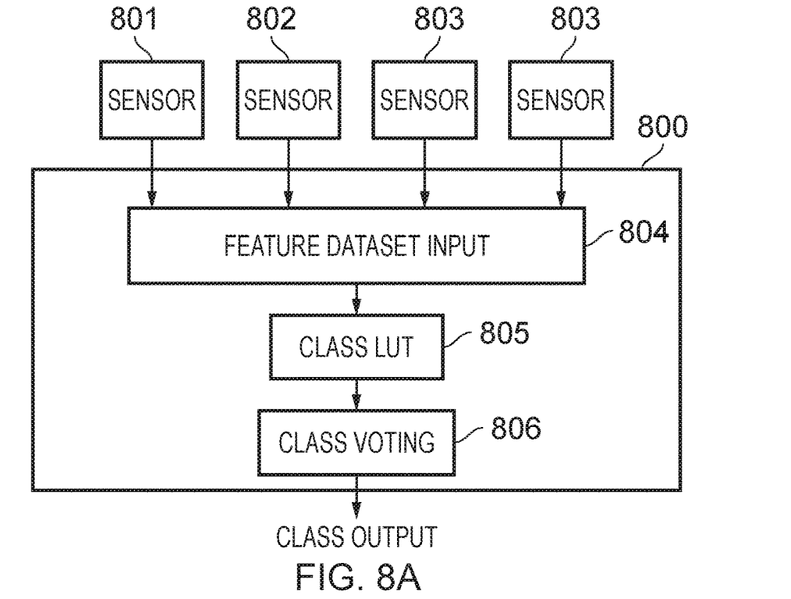
FIG. 8A schematically illustrates a set of sensors generating the input feature data set for an apparatus in some example embodiments.
Figure 8B:
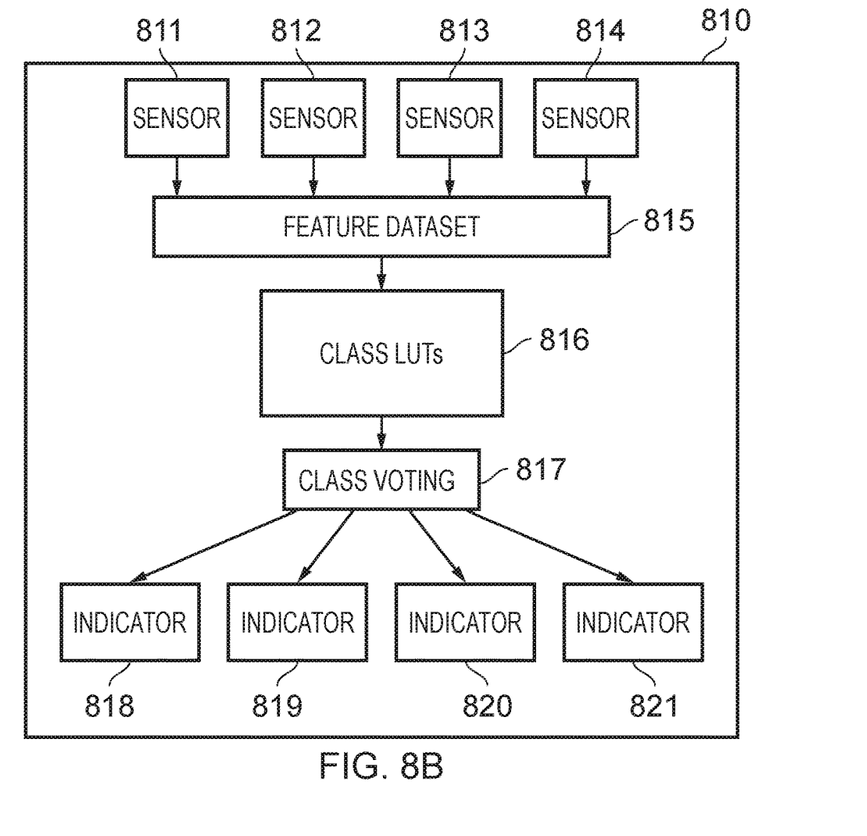
FIG. 8B schematically illustrates an apparatus embodied as a plastic fabricated device in some example embodiments.

The present techniques may find implementation in variety of contexts, but FIG. 8A gives an example of particular implementation where the feature data set is generated by a set of sensors. Accordingly, an apparatus 800 is shown which receives respective feature data values from four sensors 801-803. These are received by the feature data set input 804 which passes them to the class lookup table 805 in order for a set of four class indications to be retrieved. The class voting circuitry 806 (as described above) then selects a single one of these class indications as the final class output, here by mode voting. As in the example of FIG. 8A the sensors may be external to the apparatus but other examples are possible, one of which is illustrated in FIG. 8B. Here the apparatus 810 is a self-contained unit wherein four sensors 811-814 form part of the apparatus 810. As in the example of FIG. 8A the output of these sensors is received by a feature dataset input 815 which can temporarily hold these values before they are passed to a set of class lookup tables 816, in order for a corresponding set of class indications to be read out. These class indications are passed to the class voting circuitry 817 which then determines a single class on the basis of a vote between them. The apparatus 810 in this example further indicates four indicators 818-821 which are used by the apparatus to indicate which class was selected. Accordingly it will be understood that four different classes are defined in this example, but note that the present techniques are not constrained to this number of classes (and further that the fact that four inputs are shown from four sensors is purely coincidental). These indicators may take a variety of forms, but to name just one example may be a visual indication, e.g. illuminating a light or changing the colour of a small surface area or a different LED for each class, such that a user can perceive that on the basis of the current sensor data input a particular class has been selected. Accordingly, in such an example the class indications can characterise different situations which may be linked to different balances of sensor data input. It is to be further noted that the apparatus 810 may be physically constructed in a variety of different ways. This could for example be a small system on chip embodied in silicon, but in other examples (in particular such as will be described below with reference to FIG. 9) the apparatus may instead be embodied as a plastic fabricated device. Although according to contemporary technologies the number of logic gates which can be provided for a given area of plastic fabricated device by comparison to a silicon fabricated device is considerably lower, the particularly low gate counts which are possible according to the present techniques have been found to lend themselves particularly well to such plastic fabricated devices. The above discussed implementation shown in FIG. 7 has been implemented in hardware using such plastic technology. The class prediction can be made in 10 μs, which is 2-8× faster than a Gaussian naïve Bayes implementation. Moreover it consumes only 315 gates, which is 10-30× smaller than a Gaussian naïve Bayes implementation.

Figure 9:
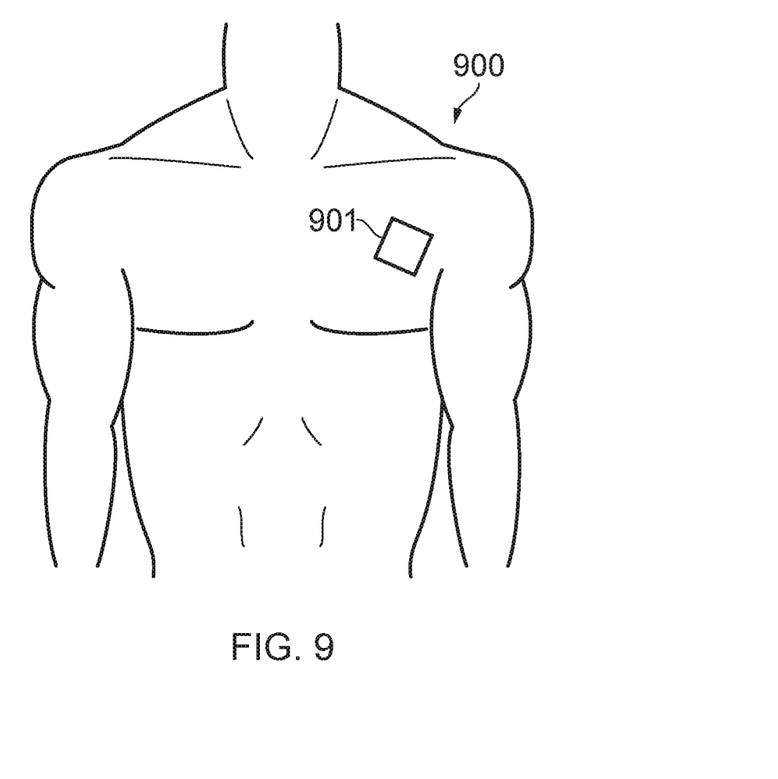
FIG. 9 schematically illustrates an apparatus designed to be a wearable device in some example embodiments.

FIG. 9 shows the torso area of a user in an example in which the apparatus may be a wearable device. Hence in this example the apparatus 901, which may for example be arranged in accordance with the example of FIG. 8B as described above, is worn on or close to the skin of a user 900. In just one example embodiment the sensors which form part of the apparatus are then configured to be responsive to local environment conditions which it is desirable to monitor. These could be variously configured from a range of known sensors. Any available sensors may be deployed here, but examples such as sensors for temperature, humidity, pressure, ECG/EMG, or the presence of particular chemicals may be contemplated. It should be noted that the position of the apparatus in the example of FIG. 9 is merely for clarity of illustration and this device could be worn in any appropriate location on or near to the skin. For example in one contemplated example the apparatus embodied as a plastic fabricated device might be worn underneath the armpit, such that a range of chemical sensors could determine the balance of chemicals present and activate one of the indicators to signal to the user a particular message about the current "chemical balance" of the under arm area.

Figure 10:
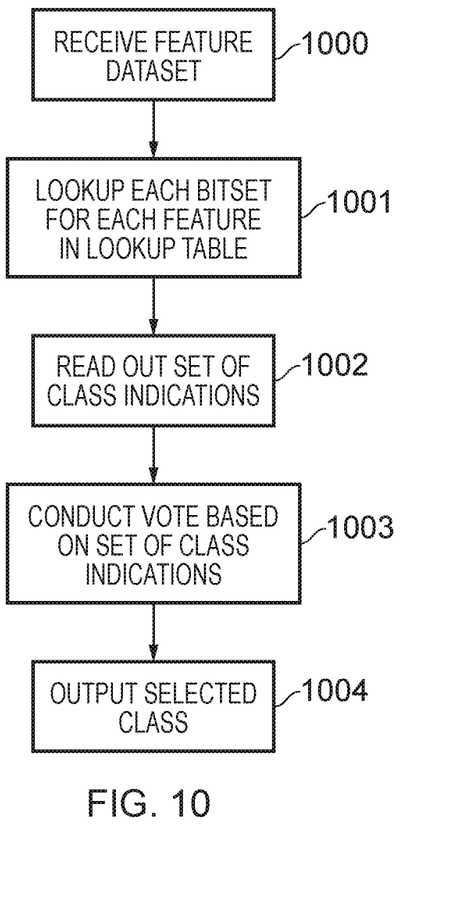
FIG. 10 shows a sequence of steps which are taken according to the method of some example embodiments.

FIG. 10 shows a sequence of steps which are taken accord to the method of one example embodiment. At step 1000 a feature data set is received and then at step 1001 each bit set (representing each feature value in the feature data set) is used to perform a lookup in a lookup table of class indications. The corresponding set of class indications is then read out at step 1002 and at step 1003 a vote is conducted based on the set of class indications read out to determine a selected class. The selected class is then output at step 1004.

In brief overall summary, apparatuses and methods of operating such apparatuses are disclosed. An apparatus comprises feature dataset input circuitry to receive a feature dataset comprising multiple feature data values indicative of a set of features, wherein each feature data value is represented by a set of bits. Class retrieval circuitry is responsive to reception of the feature dataset from the feature dataset input circuitry to retrieve from class indications storage a class indication for each feature data value received in the feature dataset, wherein class indications are predetermined and stored in the class indications storage for each permutation of the set of bits for each feature. Classification output circuitry is responsive to reception of class indications from the class retrieval circuitry to determine a classification in dependence on the class indications. A predicated class may thus be accurately generated from a simple apparatus.

In the present application, the words "configured to . . . " are used to mean that an element of an apparatus has a configuration able to carry out the defined operation. In this context, a "configuration" means an arrangement or manner of interconnection of hardware or software. For example, the apparatus may have dedicated hardware which provides the defined operation, or a processor or other processing device may be programmed to perform the function. "Configured to" does not imply that the apparatus element needs to be changed in any way in order to provide the defined operation.

Although illustrative embodiments have been described in detail herein with reference to the accompanying drawings, it is to be understood that the invention is not limited to those precise embodiments, and that various changes, additions and modifications can be effected therein by one skilled in the art without departing from the scope of the invention as defined by the appended claims. For example, various combinations of the features of the dependent claims could be made with the features of the independent claims without departing from the scope of the present invention.

The invention claimed is:

1. An apparatus embodied as a plastic fabricated device, the apparatus comprising:
    feature dataset input circuitry, included as part of the plastic fabricated device, to receive a feature dataset comprising multiple feature data values indicative of a set of features, wherein each feature data value is represented by a set of bits;
    class retrieval circuitry, included as part of the plastic fabricated device and responsive to reception of the feature dataset from the feature dataset input circuitry, to retrieve from class indications storage a class indication for each feature data value received in the feature dataset, wherein the class indications are predetermined and stored in the class indications storage for each possible value of the set of bits for each feature, and wherein the class indications storage has a look-up table format and the class retrieval circuitry is arranged to perform a look-up procedure with respect to the look-up table format for each feature data value received in the feature dataset; and
    classification output circuitry, included as part of the plastic fabricated device and responsive to a reception of the class indications from the class retrieval circuitry, to determine a classification by a vote amongst the class indications.

2. The apparatus as claimed in claim 1, wherein the class indications stored in the class indications storage for each feature are each predetermined as a best class indication which maximises a Bayes Classifier for the feature in a training phase using feature training datasets.

3. The apparatus as claimed in claim 2, wherein the Bayes Classifier is a Gaussian naïve Bayes Classifier.

4. The apparatus as claimed in claim 2, wherein the Bayes Classifier is based on a single distribution type used for each feature of the set of features.

5. The apparatus as claimed in claim 2, wherein the Bayes Classifier is based on heterogeneous distribution types used for the set of features.

6. The apparatus as claimed in claim 1, wherein the class retrieval circuitry is arranged to retrieve in parallel the class indications for each feature data value received in the feature dataset.

7. The apparatus as claimed in claim 1, wherein the class retrieval circuitry is arranged to retrieve in a serial sequence the class indications for each feature data value received in the feature dataset.

8. The apparatus as claimed in claim 1, wherein the class indications are weighted.

9. The apparatus as claimed in claim 8, wherein weights for the class indications are determined in a training phase using feature training datasets.

10. The apparatus as claimed in claim 8,
wherein the classification output circuitry is responsive to reception of the class indications from the class retrieval circuitry to determine the classification by a vote amongst the class indications,
wherein weights of the class indications are used as a tiebreaker when the vote selects more than one class indication.

11. The apparatus as claimed in claim 1, wherein each feature data value is represented by a set of fewer than 10 bits, preferably by a set of 5 bits.

12. The apparatus as claimed in claim 1, wherein the class indications are stored in the class indications storage using a representation of fewer than 5 bits, preferably using a representation of 3 bits.

13. The apparatus as claimed in claim 1, wherein the apparatus is a wearable device.

14. The apparatus as claimed in claim 1, wherein the feature dataset input is coupled to a plurality of sensors each providing a respective feature data value.

15. The apparatus as claimed in claim 1, wherein the apparatus is embodied comprising fewer than 1000 logic gates and preferably comprising fewer than 500 logic gates.

16. A method of operating an apparatus embodied as a plastic fabricated device, the method comprising:
   receiving by feature dataset input circuitry included in the plastic fabricated device at a feature dataset input a feature dataset comprising multiple feature data values indicative of a set of features, wherein each feature data value is represented by a set of bits;
   retrieving by class retrieval circuitry included in the plastic fabricated device from class indications storage a class indication for each feature data value received in the feature dataset, wherein the class indications are predetermined and stored in the class indications storage for each possible value of the set of bits for each feature, and wherein the class indications storage has a look-up table format and the retrieving, by class retrieval circuitry, comprises performing a look-up procedure with respect to the look-up table format for each feature data value received in the feature dataset; and
   determining by classification output circuitry included in the plastic fabricated device a classification by a vote amongst the class indications.

17. Apparatus embodied as a plastic fabricated device, the apparatus comprising:
   means, included as part of the plastic fabricated device, for receiving a feature dataset comprising multiple feature data values indicative of a set of features, wherein each feature data value is represented by a set of bits;
   means, included as part of the plastic fabricated device, for retrieving from means for storing class indications a class indication for each feature data value received in the feature dataset, wherein class indications are predetermined and stored in the means for storing class indications for each possible value of the set of bits for each feature, wherein the means for storing class indications has a look-up table format, and wherein the means for retrieving is arranged to perform a look-up procedure with respect to the look-up table format for each feature data value received in the feature dataset; and
   means for determining a classification by a vote amongst the class indications.

\* \* \* \* \*